US008252522B2

(12) United States Patent
Vullev et al.

(10) Patent No.: US 8,252,522 B2
(45) Date of Patent: Aug. 28, 2012

(54) SPECIES DETECTION METHODS AND SYSTEMS

(75) Inventors: Valentine Ivanov Vullev, Riverside, CA (US); Duoduo Bao, Riverside, CA (US); Marion Sheldon Thomas, Riverside, CA (US); Elizabeth Rosalyn Zielins, Coarsegold, CA (US)

(73) Assignee: The Regents of the University of California, Oakland, CA (US)

( * ) Notice: Subject to any disclaimer, the term of this patent is extended or adjusted under 35 U.S.C. 154(b) by 137 days.

(21) Appl. No.: 12/190,957

(22) Filed: Aug. 13, 2008

(65) Prior Publication Data

US 2009/0047664 A1 Feb. 19, 2009

Related U.S. Application Data

(60) Provisional application No. 60/955,769, filed on Aug. 14, 2007.

(51) Int. Cl.
*C12Q 1/70* (2006.01)
(52) U.S. Cl. .................................... 435/4; 435/5; 435/34
(58) Field of Classification Search .................. None
See application file for complete search history.

(56) References Cited

U.S. PATENT DOCUMENTS

2006/0127940 A1* 6/2006 Bao et al. .......................... 435/6

OTHER PUBLICATIONS

Guckert, et al. Phospholipid Ester-Linked Fatty Acid Profile Changes during Nutrient Deprivation of Vibrio cholerae: Increases in the trans/cis Ratio and Proportions of Cyclopropyl Fatty Acids. Appl. Environ. Microbiol.1986; 52(4):794-801.*
McHugh and Tucker. Flow Cytometry for the Rapid Detection of Bacteria in Cell Culture Production Medium. Cytometry Part A. 71A:1019-1026.*
Thomas, et al. Kinetics of Bacterial Fluorescence Staining with 3,30-Diethylthiacyanine. Langmuir. 2010. 26(12): 9756-9765.*
Ponder, J.B. Colorimetric Sensor Array: Do I See What You Smell. Final Seminar, 515 "Inorganic Seminar" (under the Guidance of K. S. Suslick and in collaboration with J.R. Carey, K.I. Hulkower, C.K. Ingison, A Sen and A.E. Wittrig, Dept. of Chemistry and Microbiology, U. Illinois, Urbana. May 8, 2006.*

* cited by examiner

*Primary Examiner* — Zachariah Lucas
*Assistant Examiner* — Stuart W Snyder
(74) *Attorney, Agent, or Firm* — Joseph R. Baker, Jr.; Gavrilovich, Dodd & Lindsey, LLP

(57) ABSTRACT

The disclosure provides methods, systems and kits for cellular and subcellular identification in a rapid, throughput manner.

6 Claims, 3 Drawing Sheets

SPECIES DETECTION METHODS AND SYSTEMS

CROSS REFERENCE TO RELATED APPLICATIONS

This patent application claims the benefit of U.S. Provisional Patent Application No. 60/955,769 filed on Aug. 14, 2007, and incorporated herein by reference in its entirety.

FIELD OF THE INVENTION

The invention relates to colorogenic, fluorescent, and luminescent assays and to cells and kits useful therein.

BACKGROUND

Bacterial infections are the cause for about a quarter of the human deaths throughout the world. For example, in the U.S.A. in the early 2000s, food-borne bacteria were the reason for about 33,000,000 illnesses per year, of which about 10,000 were fatal.

Accessible and inexpensive methodologies for fast detection and identification of bacterial species are essential for prevention and early diagnosis. Polymerase chain reaction (PCR), immunoassays, fluorescence in situ hybridization, Raman spectroscopy and impedance spectrometry are some of the methodologies used for bacterial sensing. Optical techniques based on staining of bacterial cells with fluorescent dyes have gained immense popularity due to their: (1) relative simplicity; (2) relatively high sensitivity; (3) speed of analyses; and (4) low reagent cost.

SUMMARY

This disclosure describes assays for detection and identification of bacteria (and other biological species) based on the kinetics of changes in the emission and absorption properties of staining chromophores. The changes in the following photophysical properties of the chromophores can be monitored for the assays: (1) emission quantum yields; (2) emission maxima; (3) emission lifetimes; (4) absorption extinction coefficients; and (5) absorption maxima. The disclosure demonstrates the feasibility of this assay on bacterial samples. In one aspect, the samples are stained with a fluorescent dye (e.g., that cause fluorescence enhancement of cationic dyes).

The disclosure demonstrates that the analyses of kinetics are useful for the predication of species. For example, the assays are performed by comparing the samples before and after the staining (e.g., after incubation of the sample with the staining reagents for a certain period of time). The studies indicated that there is a wealth of information in the pathways of the staining processes. For example, although two different species may manifest identical staining toward the same reagent, the kinetics of achieving the final stained state can be significantly different and will depend on the species themselves.

In many cases, treatment after the staining is required to increase the imaging contrast (i.e., wash of the non-bound chromophores). Using emission-enhancement procedures removes the need for post-staining treatment. The staining dye has strong fluorescence if bound to bacterial objects and does not fluoresce significantly if free in solution. Therefore, the free dye will not contribute to the background fluorescence and can be left in with the sample during the image and/or spectral analysis.

Certain organic chromophores, such as thioflavin T and 3,3'-diethylthiacyanine (FIG. 1a, b) can be used in the methods and system of the invention. Such chromophores manifest a significant increase in their fluorescence quantum yields when in the presence of vegetative bacteria or bacterial spores (FIG. 2). The rate constants, with which the fluorescence intensities of such chromophores increase, are characteristic of the bacterial species (FIG. 3).

Should two different species of bacteria manifest the same or similar staining kinetics toward the same dye, parallel assays with chromophores with different charge and hydrophobicity (FIG. 1) can be used. The kinetic response toward a few selected reagents will be unique for the species and can be used as "fingerprints" for their identification. This method will also allow for identification of unknown species: i.e., species for which there are no "fingerprints" in the database.

Furthermore, the described approach is quantitative. The intensity of the fluorescence enhancement is proportional to the number of chromophores bound to the bacterial species. Should the analysis is conducted with excess of staining reagent, the number of strongly fluorescent species (and the fluorescence intensity) will be proportional to the number of bacteria or other analyte species.

The disclosure provides a method of identifying a species of microorganism, comprising: contacting the microorganism with a colorogenic agent, a fluorescent agent, a bioluminescent agent or any combination thereof; measuring the kinetic change in detected agent over a period of time to provide a kinetic profile; and comparing the kinetic profile to a known profile, wherein a similarity in kinetic profile to known profile is indicative of the species of microorganism.

The disclosure also provides a method of identifying a cellular or subcellular entity comprising: obtaining kinetic measurements of changing spectroscopic characteristics of chromophores during their interaction with the cellular and subcellular entities; comparing the kinetic measurements to known controls, wherein a similar kinetic measurement is indicative of the cellular or subcellular species.

The disclosure also provide kits for carrying out the method of the disclosure.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
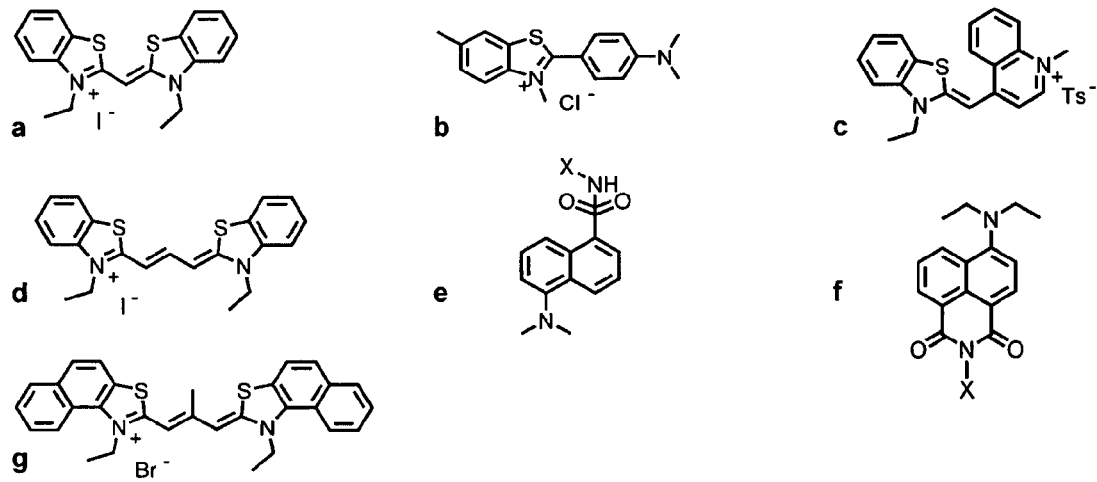
FIG. 1 shows cationic and neutral dyes useful for fluorescence staining: (a) 3,3'-Diethylthiacyanine iodide; (b) thiophlafin T; (c) thiazole orange T; (d) 3,3'-Diethylthiacarbocyanine iodide; (e) dansylamide; (f) 4-diethylaminonaphthalic imide; (g) "stain all".
Figure 2:
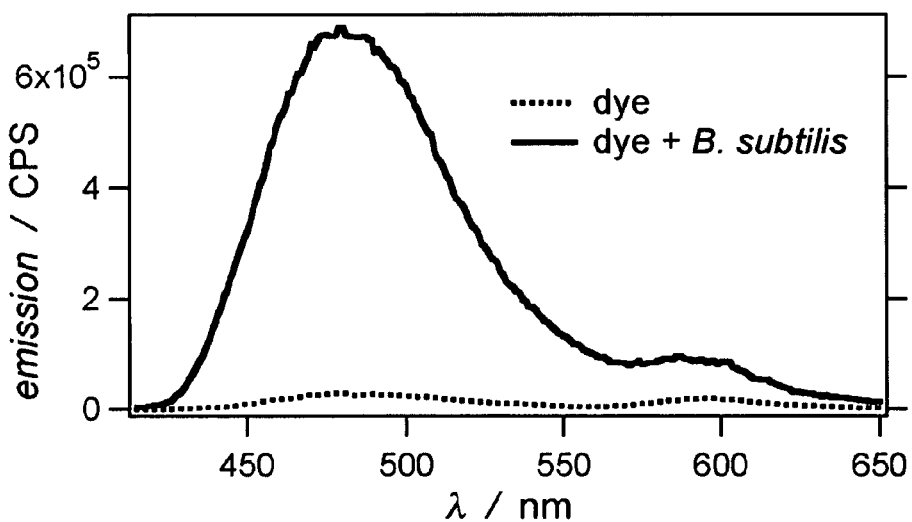
FIG. 2. Emission spectra of 6.4 μM benzothazole dye, 3,3'-Diethylthiacyanine iodide (THIA), in 2 mM TRIS buffer, pH=8.5, in the presence and absence of bacteria (*Bacillus subtilis*, $10^5$ cell/mL). The long-wavelength peak, at 590 nm, is a result of excimer fluorescence. Monitoring the changes in the monomer and excimer fluorescence simultaneously, provides an additional parameter for increase in the specificity of the assay.

As used herein and in the appended claims, the singular forms "a," "and," and "the" include plural referents unless the context clearly dictates otherwise. Thus, for example, reference to "a cell" includes a plurality of such cells and reference to "the agent" includes reference to one or more agents known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Since the development of the Gram stains, the identification of the bacterial species using staining techniques has been based solely on the initial and final appearance of the cells (i.e., before and after the staining process). Hence, the staining analyses produce only Boolean outcomes: i.e., the reagents either stain (positive), or do not stain (negative) the analyzed bacteria. This positive/negative indication provides information on the "presence" of bacteria but is limited to the identification of the type of bacteria. This is due, in part, to the fact that many of the stains used can cross stain various species of organism.

Techniques, such as immunoassays, have the specificity to identify the presence of specific bacterial species. Unfortunately, for such techniques, only the species that are searched for are detected. Hence, the presence of other bacterial species, which are not targeted by the particular immunoassay, will remain undetected. Furthermore, reagents for such assays are somewhat costly and not available for many bacterial species that are potentially a health hazard.

The kinetics of staining encompasses the rates of color change (colorometric) and/or the rates of appearance of fluorescence or luminescence resultant from the migration of the dyes from the solvent into the cell walls and/or to the cell interior. The kinetics of staining is dependent on the type of the species (e.g., bacterial species). For example, two different types of bacteria may have the same appearance (spectrum and image) after the completion of the staining. These two bacterial species, however, may manifest significantly different kinetics of the spectral changes leading to the same final appearance. Therefore, time-resolved analytical techniques that are based on the kinetics of spectral changes will considerably broaden the capabilities of the staining methodologies. In addition to the Boolean distinction based on "positive" and "negative" stains, the kinetic signatures of the staining processes will provide further means for discernment among "positively"-stained bacterial species.

Any number of cellular and subcellular entities can be identified by the methods, systems and kits of the disclosure. The methods, systems and kits are applicable to prokaryotic, eukaryotic, viral, prion and subcellular organelle detection and identification. Bacteria that can identified by the methods of the disclosure include both gram-negative and gram-positive bacteria. For example, bacteria include *Staphylococcus aureus, Streptococcus pyogenes* (group A), *Streptococcus* sp. (viridans group), *Streptococcus agalactiae* (group B), *S. bovis, Streptococcus* (anaerobic species), *Streptococcus pneumoniae*, and *Enterococcus* sp.; Gram-negative cocci such as, for example, *Neisseria gonorrhoeae, Neisseria meningitidis*, and *Branhamella catarrhalis*; Gram-positive bacilli such as *Bacillus anthracis, Bacillus subtilis, P. acne, Corynebacterium diphtheriae* and *Corynebacterium* species, which are diptheroids (aerobic and anerobic), *Listeria monocytogenes, Clostridium tetani, Clostridium difficile, Escherichia coli, Enterobacter* species, *Proteus mirablis* and other sp., *Pseudomonas aeruginosa, Klebsiella pneumoniae, Salmonella, Shigella, Serratia*, and *Campylobacter jejuni*. Infection with one or more of these bacteria can result in diseases such as bacteremia, pneumonia, meningitis, osteomyelitis, endocarditis, sinusitis, arthritis, urinary tract infections, tetanus, gangrene, colitis, acute gastroenteritis, impetigo, acne, acne posacue, wound infections, borne infections, fascitis, bronchitis, a variety of abscesses, nosocomial infections, and opportunistic infections. Fungal organisms may also identified by the methods of the disclosure and include dermatophytes (e.g., *Microsporum canis* and other *Microsporum* sp.; as well as *Trichophyton* sp. such as *T. rubrum*, and *T. mentagrophytes*), yeasts (e.g., *Candida albicans, C. Tropicalis*, and other *Candida* species), *Saccharomyces cerevisiae, Torulopsis glabrata, Epidermophyton floccosum, Malassezia furfur* (*Pityropsporon orbiculare*, or *P. ovale*), *Cryptococcus neoformans, Aspergillus fumigatus, Aspergillus nidulans*, and other *Aspergillus* sp., Zygomycetes (e.g., *Rhizopus, Mucor*), *Paracoccidioides brasiliensis, Blastomyces dermatitides, Histoplasma capsulatum, Coccidioides immitis*, and *Sporothrix schenckii*.

In one aspect, assays for bacterial identification based on the kinetics of fluorescence staining, utilize chromophores that show: (1) negligible fluorescence in aqueous media; and (2) at least an order of magnitude increase in their emission quantum yields upon binding to certain bacterial species. Chromophores with flexible π-conjugated sections in their molecules (FIG. 1*a-d, g*) tend to manifest such emission enhancement when transferred from aqueous media to the relatively more rigid microenvironment of bacterial walls. In this case, the fluorescence enhancement results from suppression of vibrational pathways that compete with the light-radiative transitions to the ground state. Using dyes that manifest such emission enhancement will create a contrast with minimum background fluorescence, eliminating the need for treatment of the samples for increasing the contrast after the staining.

Alternatively, for kinetic assays chromophores that manifest 50-100 nm emission spectral shifts upon transition from aqueous environment to a relatively non-polar environment of the cell wall can be used (FIG. 1*e, f*). In this case, the emission changes are results from the change in the polarity, rather than viscosity, of the microenvironment. Chromophores with ground and excited states that have significantly different electrical dipole moments will exhibit such trends and are possible candidates for emission photoprobes.

In one aspect, combining of historical approaches and a combination of the approaches using parallel kinetic assays will yield unique "signatures" for various species discerning them based on the rigidity and the polarity of the cellular wall, membrane or intracellular environment.

The described kinetic assay will have certain specificity and ability to discern between cell species (e.g., bacterial species). In addition, the methods and systems will still give signals if unknown types of bacteria are present. The simplicity of the proposed methodology will make it readily adoptable for clinical diagnoses and monitoring applications.

"Bioluminescence" means light emission in a living cell wherein the light emission is dependent upon and responsive to metabolic activity.

"Bioluminescent marker" means a nucleotide sequence or polypeptide that, when incorporated into a cell and expressed, causes bioluminescence during metabolic activity of the cell.

The term "colorogenic" refers to a composition that generates a colored composition or a colored composition that exhibits a change in its absorption spectrum upon interacting with another substance, for example, upon binding to a biological compound or metal ion, upon reaction with another molecule or upon metabolism by an enzyme. In some aspects, colorogenic labels result in a detectable precipitate.

The term "fluorescent" refers to a marker that absorbs light a first excitation spectrum and emits light at a second different emission spectrum. A given fluorescent molecule is characterized by an excitation spectrum (sometimes referred to as an absorption spectrum) and an emission spectrum. When a fluorescent molecule is irradiated with light at a wavelength within the excitation spectrum, the molecule fluoresces, emitting light at wavelengths in the emission spectrum for that particular molecule. Thus when a sample is irradiated with excitation light at a wavelength that excites a certain fluorescent molecule, the sample containing the fluorescent molecule fluoresces. If this is performed continuously changes in fluorescence over time can be measured, thus providing information regarding the rate of change or absorption of fluorescent molecule. In some instances the light emanating from the sample and surrounding area may be filtered to reject light outside a given fluorescent agent's emission spectrum. Thus an image acquired from a sample contacted with an agent comprising a fluorescent label shows only objects of interest in the sample that bind or interact with the fluorescently labeled agent.

A fluorescent indicator should have distinguishable excitation and emission spectra. Where two or more fluorescent indicators are used they should have differing excitation and emission spectra that differ, respectively, by some minimal value (typically about 15-30 nm). The degree of difference will typically be determined by the types of filters being used in the process. Typical excitation and emission spectra for DAPI, FITC, Cy3, Cy3.5, Cy5, CyS.5, and Cy7, as well as the agents provided in FIG. 1 are known. Fluorescence can be measured by optical arrays. For example, an apparatus useful for measuring fluorescence can include a fluorescent excitation light source and may further include a plurality of fluorescent filters. Alternatively, a filter wheel may have an electronically tunable filter. In one aspect, fluorescent excitation light from a fluorescent excitation light source passes through a fluorescent filter and proceeds to contact a sample. Fluorescent emission light emitted from a fluorescent agent contained in a sample passes to an optical sensing array. The fluorescent emission light forms an image, which is digitized by an optical sensing array, and the digitized image is sent to an image processor for subsequent processing.

In one aspect, the disclosure can use a colorogenic detectable signal. A number of enzymatic colorogenic assays can be used in the methods of the disclosure. Changes in a detectable signal can be measured over a period of time to provide a rate of change, absorption minimum and maximum. In another aspect, a combination of detectable signals can be used. For example, a combination of bioluminescence methods, fluorescence methods, colorogenic methods and any combination thereof can be used. It will be appreciated by those with skill in the art, based upon the disclosure, that any suitable bioluminescent, fluorescence or colorgenic marker may be used in the practice of the disclosure. It will be further appreciated that the type of bioluminescent, colorogenic or fluorescence marker used may, in part, depend upon the types of cells used in the practice of the disclosure. An exemplary bioluminescent marker for use in the methods of the disclosure includes the firefly luciferase (luc) gene (GeneBank accession number AAA89084) driven by a constitutive glyceraldehyde-3-phosphate dehydrogenase (GPD) promoter. The bioluminescence catalyzed by the luc gene requires the substrate (luciferin) and energy in the form of endogenous ATP. So long as the medium in which the cells grow contains luciferin as a supplement, the bioluminescence of cells is dependent on the availability of intracellular ATP. Since the intracellular ATP concentration is dependent on energy metabolism, the bioluminescent output represents the level of metabolic activities of the cell as well as the rate of synthesis, uptake through the cell membrane or cell wall; the kinetics of which will vary upon cell types.

Other bioluminescent markers that may be used in the methods and cells of this disclosure are known to those with skill in the art or will be apparent to them based upon the present disclosure. For example, Bronstein et al. (1994) describe bioluminescent markers that may be used in this disclosure. For combination assays, the bioluminescent markers, fluorescent and colorogenic makers that are used in the methods and cells of the disclosure may be incorporated into a cell by inserting the polynucleotide encoding such markers into an appropriate vector followed by contact with an appropriate substrate (the diffusion of which will vary and provide kinetic fingerprint information). Such vectors may be designed so that they are stably incorporated into the chromosomal DNA of a cell or they may be designed to express the applicable marker without chromosomal integration. Alternatively, the cell can be exposed to the fluorescent, bioluminescent or colorogenic marker directly and the uptake and detectable signal measured.

Expression vectors containing the necessary elements for transcriptional and translational control of the inserted coding sequence in a cell may be used to incorporate into a cell a biologically active enzyme (for generation of a colorogenic signal), a bioluminescent marker, or fluorescent marker and the like. The transcriptional and translational control elements include regulatory sequences, such as enhancers, constitutive and inducible promoters, and 5' and 3' untranslated regions in the vector and in polynucleotide sequences encoding the applicable marker. Such elements may vary in their strength and specificity. Specific initiation signals may also be used to achieve more efficient translation of sequences encoding the markers. Such signals include the ATG initiation codon and adjacent sequences, e.g. the Kozak sequence. In cases where sequences encoding a marker and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994)).

Methods which are well known to those skilled in the art based upon the disclosure may be used to construct expression vectors containing polynucleotides encoding colorogenic enzymes, bioluminescent markers or fluorescent markers and appropriate transcriptional and translational control elements.

As those skilled in the art will recognize based upon the disclosure, a wide variety of cloning vectors may be used as vector backbones in the construction of a vector of the disclosure, including pBluescript-related plasmids (e.g., Bluescript KS+11), pQE70, pQE60, pQE-9, pBS, pD10, phagescript, phiX174, pBK Phagemid, pNH8A, pNH16a, pNH18Z, pNH46A, ptrc99a, pKK223-3, pKK233-3, pDR540, and pRIT5 PWLNEO, pSV2CAT, pXT1, pSG (Stratagene), pSVK3, PBPV, PMSG, and pSVL, pBR322 and pBR322-based vectors, pMB9, pBR325, pKH47, pBR328, pHC79, phage Charon 28, pKB11, pKSV-10, pK19 related plasmids, pUC plasmids, and the pGEM series of plasmids. These vectors are available from a variety of commercial sources (e.g., Boehringer Mannheim Biochemicals, Indianapolis, Ind.; Qiagen, Valencia, Calif.; Stratagene, La Jolla, Calif.; Promega, Madison, Wis.; and New England Biolabs, Beverly, Mass.). However, any other vectors, e.g. plasmids, viruses, or parts thereof, may be used so long as they are replicable and viable in the desired host. The vector may also comprise sequences which enable it to replicate in a host cell whose genome is to be modified. The use of such a vector can expand the interaction period during which recombination can occur, increasing the efficiency of targeting (see Ausubel et al (2003), Unit 9.16, FIG. 9.16.1).

Cells to be used in the practice of the methods of the disclosure may be stored and cultured according to methods well known to those with skill in the art based upon the present disclosure. For example, mammalian cells may be cultured according to methods described in Bonifacino et al. (2003), Chapter 1. Yeast cells may be cultured according to general methods described in Ausubel et al. (2003), Chapter 13. Bacterial samples may be cultured as known in the art following sampling from an environment or subject.

In the practice of the methods of the disclosure, the contacting of cells with a labeling agent (e.g., a colorogenic agent, luminescent agent, bioluminescent agent or any combination thereof) may be employed according to methods known by those with skill in the art based upon the disclosure. The method used will depend upon many variables, including the types of cells used.

In one embodiment, yeast cells (e.g., *Saccharomyces cerevisiae*) are treated with labeling agent in 96 well plates for about 17 hours at about 30° C. Following contacting of the cells with the labeling agent, the cells are monitored for changes in the detectable label. The initial absorption or emission, the change of absorption or emission and the final absorption and emission are monitored and recorded. This information is then compared to the same information from a control comprising a defined cellular population and species. The experimental value are then measured with standardized controls and if the information comprising the kinetic changes, initial values and final values are similar, the experimental population is indicated as being indicative of the standardized control species or population. Similar techniques can be used in the case of a bacterial species or population.

For high throughput detection, cells may be plated on multi-well plates (e.g., 12, 24 or 48, 96, or 384 wells). Bioluminescence may be visualized using any light detection device, for example, a Lumi-Imager® F1 photon-counting device (Roche Diagnostics, Indianapolis, Ind.) that may be used to identify colonies in multi-well plates. Other light detection devices that may be used include NightOwl (Berthold, Germany) and Kodak IS1000 (Kodak, Rochester, Md.). Furthermore, the digital image of bioluminescent colonies of cells is suitable for automated data evaluation using image analysis software (for example, Image Plus PrO™, ver. 4.1 (Media Cybernetics, Inc., Carlsbad, Calif.).

For expedience and high throughput, the described kinetic spectroscopic assays can be incorporated in multiplate reader and/or microfluidic systems. Relatively simple and enclosed microfluidic systems will allow portability and field use, appropriate for environmental control and pathogen detection. For example, polydimethylsiloxane (PDMS) microfluidic chips fabricated by soft lithography have been extensively used in chemical, biomolecular and cellular analysis.

Microfluidic channels can be formed in any number of materials. Thus, the devices of the disclosure include at least one flow channel that allows the flow of sample to other channels, components or modules of the system. As will be appreciated by those in the art, the flow channels may be configured in a wide variety of ways, depending on the use of the channel. For example, a single flow channel starting at a sample inlet port may be separated into a variety of smaller channels, such that the original sample is divided into discrete subsamples for parallel processing or analysis. Alternatively, several flow channels from different modules, for example, the sample inlet port and a reagent storage module (e.g., a fluorescent labeling material) may feed together. As will be appreciated by those in the art, there are a large number of possible configurations; what is important is that the flow channels allow the movement of sample and reagents from one part of the device to another. For example, the path lengths of the flow channels may be altered as needed; for example, when mixing and timed reactions are required, longer flow channels can be used.

In one embodiment, the devices of the disclosure include at least one inlet port for the introduction of a sample to the device. This may be part of or separate from a sample introduction or a sample mixing chamber.

In another aspect of the invention, the devices of the invention may include a manipulation chamber that allows for the mixing of reagent and sample.

In addition to individual straight channels, a functional microfluidic circuit often consists of channel junctions. The positioning of liquid flow at channel junctions can include valve systems.

A fluid device of the disclosure comprises a substrate (which may be one or more substrates associated with one another to define fluid channels there between). The fluid device can comprises a sample inlet in fluid communication with sample fluid flow channel and buffer inlet in fluid communication with buffer fluid flow channel.

In one embodiment, substrate comprises an insulating (e.g. glass or polymer), or a semiconducting (e.g. silicon structures) in which various features (e.g., channels, chambers, valves and the like) are designed. Such features can be made by forming those features into a surface and/or a subsurface structure of substrate using microfabrication techniques known to those skilled in the art. In one aspect, the substrate is transparent with minimal light adsorption for light detection/emission by labeling/dye reagents of the disclosure.

By extending the above channels and adding more sorting regions downstream, the disclosure provides sorting devices with multi-stage analysis. In one aspect, the disclosure provides methods and systems that utilize massive parallelism and multistaging. This allows full utilization of the central benefits of microfabrication technology to achieve high throughput, purity and recovery simultaneously.

Microfabrication technologies provide the ability to implement multiple staging and massive parallelism on a single chip, thus allowing for the production of inexpensive, disposable, flexible, and portable devices.

The above-described assay methods are for illustrative purposes only. Those with skill in the art will appreciate based upon the disclosure that a variety of assay formats may be utilized in the practice of this invention. Variations may be made based upon the types of cells, colorogenic markers, fluorescent markers, luminescent markers, the combination of markers and test, methods of contacting and culturing cells and methods of detection of labels.

The following Examples are to be construed as merely illustrative of the practice of the invention and not limitative of the remainder of the disclosure in any manner whatsoever.

EXAMPLES

The data demonstrate observed increases in the fluorescence intensity of aqueous solutions of numerous benzothiazole dyes when mixed with suspension of bacterial spores or vegetative bacteria. Microscopy observations showed high-contrast fluorescence staining of bacteria with benzothiazole dyes. The dye present in the extracellular aqueous environment does not produce background fluorescence strong enough to interfere with the image contrast. The possible reasons of this observations are: (1) the emission quantum yield of the dye bound to the bacteria is at least an order-of-magnitude larger than the fluorescence quantum yield of the free dye in the aqueous environment; and/or (2) the local concentration of the dye bound to the bacteria is larger than the concentration of the dye in the solution.

A solution of a benzothiazole dye, THIA, was used (FIG. 1*a*), in a continuous-flow microfluidic device for detection of bacterial species, as described for a terbium (III) different emission assay. Steady-state measurements show about an order of magnitude increase in the emission intensity of THIA in the presence of bacterial spores. The emission intensity of THIA is even higher when incubated with the same concentration of vegetative bacteria. Measurements with the microfluidic device, however, show a signal from the bacterial spores that is about 13 times stronger then the signal from the vegetative bacteria.

This discrepancy between the steady-state emission measurements and the microfluidic sensing is due to the difference in the kinetics of emission enhancement of THIA in the presence of vegetative bacteria and in the presence of bacterial spores. For the steady-state experiments the dye is mixed with the samples and allowed to incubate for five minutes. In the microfluidic device, however, the dye is mixed with the bacterial sample and carried to the area for emission detection in about few seconds after the mixing.

Fluorescence kinetic measurements showed that while the emission enhancement of THIA by bacterial spores occurs within the duration of the mixing (within a second or less), the intensity of the emission of THIA continues to increase for several minutes after the initial mixing of the dye with vegetative bacteria.

The microfluidic devices offer an advantage of small reagent consumption, ultrafast mixing and kinetic measurements with steady-state light sources and detectors. In addition, microfluidics will allow the merging of the kinetic assay with flow cytometry and/or single-cell kinetic analysis, which will significantly broaden its applicability for monitoring, diagnostics and analysis in clinical and research environment.

Comparison between the kinetic responses for the different bacteria species toward a fluorescence dye (FIG. 3), allows us to represent this interaction with two consecutive steps as shown on Scheme 1 (FIG. 4).

Although Scheme 1 (FIG. 4) represents a somewhat simplified model of the processes leading to the fluorescence enhancement, it is a good starting point for building a library of kinetic responses toward various fluorophores for the assays.

To simplify the kinetic analysis, the assays can be conducted under two types of extreme conditions that will assure that the first step, k1, can be approximated to pseudo-first-order process: (1) the dye is in excess to the binding sites on the bacterial surface; or (2) the binding sites on the bacterial surface are in excess to the dye. Under such conditions, the kinetics of fluorescence enhancement should manifest bi- (or multi-) exponential rises:

$$F = F_M - \sum_i F_i \exp\left(-\frac{t-\delta_t}{\tau_i}\right) \quad \text{(eq. 1)}$$

where FM is the maximum fluorescence intensity (the saturation level on the curves); $d_t$ is the injection time; $F_i$ are the pre-exponential coefficients; and $t_i$ are the time constants for the various processes: $\tau_i=1/k_i$. The above function was used for biexponential fits (i=1 and 2) for the observed kinetic data (FIG. 3).

FIG. 3 shows examples for emission-enhancement kinetics for three different bacterial species. The samples are illuminated at a region where the staining dye absorbs and the emission is monitored (the fluorescence intensity is recorded every second) at the wavelength maximum of the fluorescence spectrum of the dye (FIG. 2). After the injection of the bacteria into the dye solution (~50 s after the initiation of the data acquisition), the emission intensity increases until it plateaus at a maximum. This plateau emission maximum is what is measured with the regular staining procedures.

It is clear that all three species give positive response to the staining with this particular dye, THIA (FIG. 1*a*). The final (plateau) emission intensity for *E. coli* is smaller than the intensity for the other two bacilli. The two bacilli, however, exhibit the same final emission intensity. Therefore, regular staining techniques cannot discern between the two bacilli. Furthermore, the bacilli have identical shapes and hence, they cannot be discerned by imaging.

Using regular staining approaches based on spectroscopic techniques (i.e., on the difference in the emission intensity before and after the staining) will not provide means for facile distinguishing the *E. coli* from the bacilli (all three species give positive staining reaction). Imaging is required to differentiate between the *E. coli* and the two bacilli samples.

The emission enhancement kinetics, i.e., the rates at which the emission maxima (the plateau values for the emission intensities) are reached, is different for the three species. For quantitative comparison, the rate constants, k, and/or the time constants, τ, for the emission enhancement are extracted from the data (k=1/τ). The data points, representing the measured emission-intensities at different times, are the gray dots on FIG. 3. Using "least-square" algorithm, the data are fit to a biexponential function of fluorescence vs. time (eq. 1). The two time constants, $\tau_1$ and $\tau_2$, are two of the five fitting parameters. (The fluorescence intensity is proportional to the concentration of the dye bound to the bacteria. The exponential dependence of the bound-dye concentration on the time through the reaction comes from solving the differential rate equation for such processes.)

The fitting procedure usually lasts a few seconds. It is a standard approach for extracting of reaction rate or time constants from time-resolved data for kinetic analysis. The data fitting can carried with any commercial software for data analysis: MathLab, Igor Pro, etc.

Scheme 1 depicts the physical meaning of the two time constants of the emission-enhancement curves shown on Figure. The shorter time constants, $\tau_1$, represent the initial mixing and binding of the dye onto the surface of the bacteria. $\tau_1$ usually depends on the experimental settings and ranges between 2 and 3 s for the three species. The longer time constants, $\tau_2$, offer means for distinction between the different bacterial species.

Upon mixing of a dye with the bacterial species, the dye adsorbs to the surface of the bacterial species. This change in the microenvironment of the chromophore causes an increase in its fluorescence quantum yield. It is the faster of the two steps of the emission enhancement process ($k_1$ on Scheme 1 and $\tau_1$ on FIG. 3).

In the case of vegetative bacteria, the dye can migrate further from the surface of the cell wall into the lipid bilayer or even into the interior of the bacterial cell where it docks into a more fluorogenic microenvironment. This additional change in the microenvironment results in further increase in the emission quantum yield of the fluorophores ($k_2$ on Scheme 1).

Figure 3:
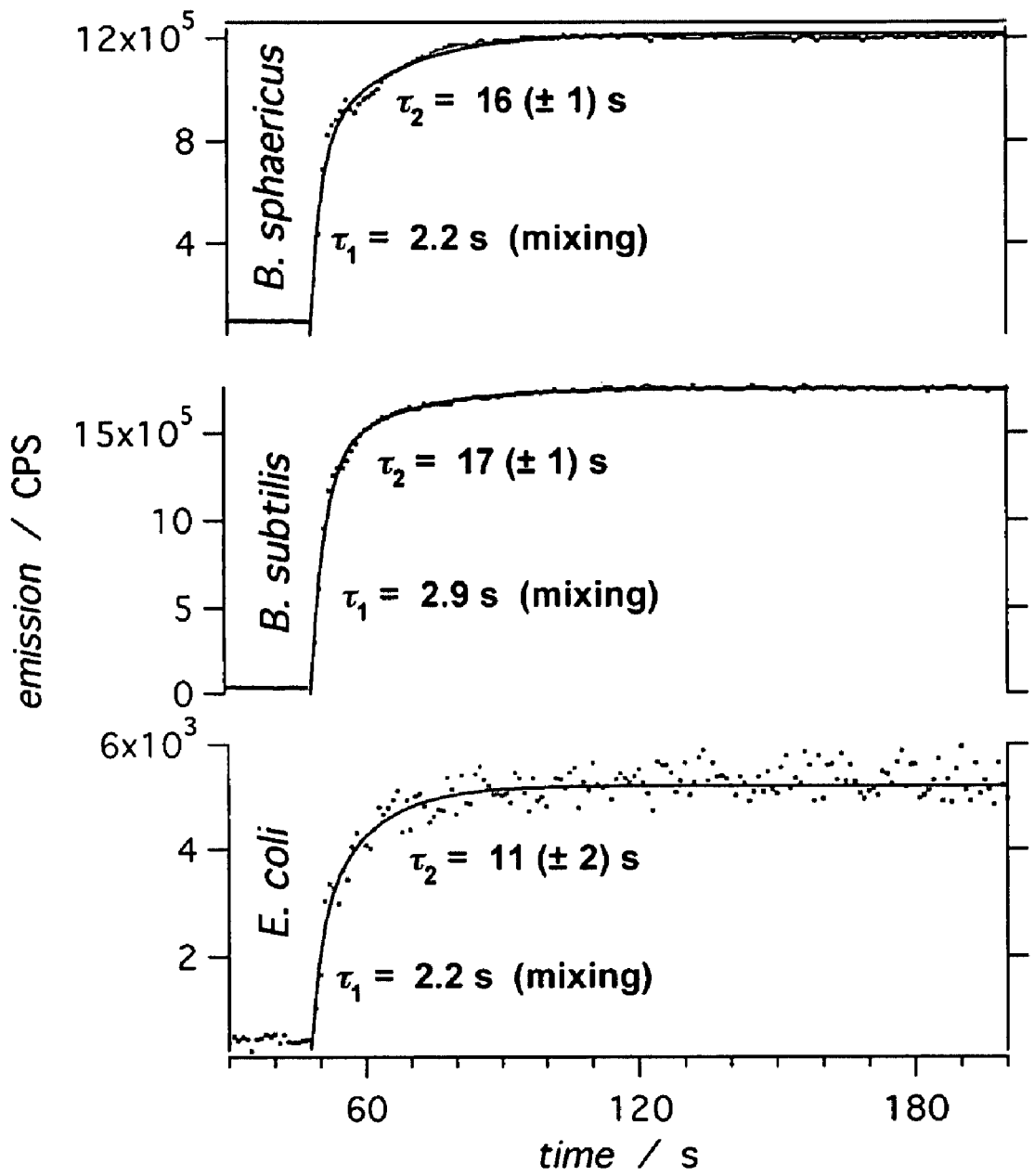
FIG. 3. Kinetics of fluorescence enhancement of 64 μM THIA in the presence of different bacteria ($10^6$ cell/mL) in TRIS buffer, pH=8.5 ($\lambda_{ex}$=420 nm, $\lambda_{em}$=470 nm). The time constants, τ, are inversely proportional to the rate constants, k=1/τ. The biexponential data fits assume pseudo-first-order processes. At about 50 s into the data acquisition, the bacteria are injected and into a stirred solution of the dye. The initial fast rise, with k between 0.3 and 0.5 s$^{-1}$, corresponds to the initial mixing and binding of the dye to the bacteria. (Although the chosen bacteria are BSL I non virulent organisms, they can serve as models for pathogen species.)
Figure 4:
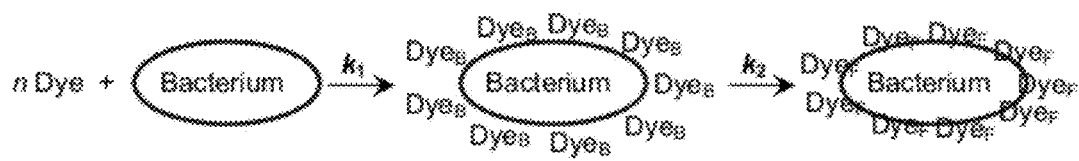
FIG. 4 shows Scheme I, which depicts Interaction between a fluorescent dye and bacterial species: free dye in solution (Dye); dye bound to bacteria (DyeB); and bound dye with increased fluorescence quantum yield (DyeF).

For vegetative bacteria $k_1$ is significantly larger than $k_2$, resulting in the observed fast increase in the emission intensity upon mixing of the bacteria with the dye, which is followed by further gradual increase in the emission intensity that proceeds for minutes (FIG. 3).

The relatively high density of the coatings of the bacterial spores probably prevents the inward migration of the adsorbed dyes, suppressing the second step of the process ($k_2$) and hence, the further increase in the fluorescence intensity. Therefore, for bacterial endospores, the second step probably does not occur, i.e., $k_2=0$. As a result, a sharp increase in the emission intensity during the mixing is observed followed by a time-independent signal.

There can be several explanations for the observed relatively slow process ($k_2$) in the kinetics pattern of emission enhancement caused by vegetative bacteria. For example, the slower of the two steps in the emission enhancement, $k_2$, can be a result from migration of the dye to the interior of the cell. Many of the staining dyes investigated are known to bind strongly to double-stranded DNA. If the quantum yield of the fluorophore, DyeB, bound to the bacterial wall is smaller than the quantum yield of the fluorophore, DyeF, bound to a DNA double strand, the migration of the staining dye to the interior of the cell where it can bind to a DNA molecule will result in the observed emission enhancement.

A number of embodiments have been described. Nevertheless, it will be understood that various modifications may be made without departing from the spirit and scope of the description. Accordingly, other embodiments are within the scope of the following claims.

What is claimed is:

1. A method of identifying a species of microorganism, comprising:
   contacting an intact microorganism with a colorogenic agent, a fluorescent agent, a bioluminescent agent or any combination thereof;
   measuring the kinetic change in detected agent over a period of time to provide a kinetic profile; and
   comparing the kinetic profile to a known profile, wherein a similarity in kinetic profile to known profile is indicative of the species of microorganism.

2. The method of claim 1, wherein the intact microorganism is a bacteria.

3. The method of claim 2, wherein the bacteria is gram negative.

4. The method of claim 1, wherein the intact microorganism is a eukaryotic cell.

5. The method of claim 1, wherein the fluorescent agent is a dye set forth in FIG. 1.

6. The method of claim 1, wherein the method is carried out in a microfluidic device.

* * * * *